United States Patent [19]

McVey

[11] 4,265,621
[45] May 5, 1981

[54] TIP FOR DENTAL ASPIRATOR

[76] Inventor: Kenneth E. McVey, Paulsen Medical and Dental Bldg., Spokane, Wash. 99201

[21] Appl. No.: 86,583

[22] Filed: Oct. 19, 1979

[51] Int. Cl.³ .............................................. A61C 17/04
[52] U.S. Cl. ..................................... 433/91; 128/276; 15/422
[58] Field of Search ..................... 433/91, 92, 93, 94, 433/95, 96; 128/276, 277; 15/422, 420, 421, 415

[56] References Cited

U.S. PATENT DOCUMENTS

| 1,698,331 | 1/1929 | Gunter | 433/94 |
| 2,210,030 | 8/1940 | Ellis | 15/420 |
| 2,637,106 | 5/1953 | Otis | 433/91 |
| 2,742,701 | 4/1956 | Berger | 433/96 |
| 3,066,672 | 12/1962 | Crosby, Jr. et al. | 128/276 |
| 3,299,511 | 1/1967 | Hutson | 433/91 |
| 3,460,255 | 8/1969 | Hutson | 433/91 |
| 3,541,583 | 11/1970 | Deuschle | 433/91 |
| 4,158,916 | 6/1979 | Adler | 433/91 |

*Primary Examiner*—Gene Mancene
*Assistant Examiner*—John J. Wilson
*Attorney, Agent, or Firm*—Wells, St. John & Roberts

[57] ABSTRACT

A removable protective tip for placement over the outer end of a dental aspirator. The tip includes a cylindrical sleeve that frictionally fits over the walls of the aspirator end, and an integral open mesh screen extending across one end of the sleeve in a plane complementary to the outer edge of the aspirator. Side vents are provided immediately adjacent the screen. The tip prevents larger objects from being drawn into the aspirator assembly and also prevents the aspirator from grasping soft tissue in the mouth.

1 Claim, 6 Drawing Figures

TIP FOR DENTAL ASPIRATOR

BACKGROUND OF THE INVENTION

This invention relates to an improvement in a dental aspirator. A modern dental aspirator is a vacuum device in the form of a short length of rigid tubing that is hand-held by the dentist or dental assistant. The outer end of the tube is projected into the mouth of a patient adjacent the area being worked upon. The remaining end of the tube is attached by a hose to a source of vacuum pressure, often located at a remote location in the building where it is used. Considerable vacuum pressure is applied to the aspirator in order to enable it to quickly draw off saliva, foreign bodies and the large quantities of water necessary for cooling purposes when using modern high speed drills.

One of the difficulties encountered by dentists when using an aspirator is the tendency of the tip to grasp or cling to soft tissue about the tongue or the lining and floor of the mouth. This not only is extremely painful to the patient, but momentarily prevents the aspirator from assuming its normal function in drawing away fluids, since the tip of the aspirator is temporarily blocked by the grasped tissue. Another problem is the tendency of the aspirator to draw away solid objects, sometimes including inlays, caps, filling materials, bridge facings, and other items which might be accidentally drawn from the mouth during dental operations.

The solution to these common problems as posed by the present disclosure is a relatively simple mesh tip designed specifically for use on an aspirator tube. The tip is in the form of a cylindrical sleeve that fits snugly about the outside walls of the aspirator at its functional end. A transverse open mesh screen formed integrally with the sleeve extends across the sleeve in an angular attitude complementary to the edges at the outer end of the aspirator. The screen can be either diagonally slanted or perpendicular to the axis of the sleeve and aspirator tube. The screen prevents large items from being drawn into the tube and also prevents the buildup of substantial vacuum pressure on the soft tissues in the mouth so as to enable the user to readily release the tube from surrounding tissue areas.

The present disclosure relates to an improved tip for the hand held aspirator, including vents adjacent to the open mesh screen designed to relieve any vacuum pressure that might otherwise develop across the end of the tip and screen should the tip become momentarily attached to tissue within the mouth. The vents are in close proximity to the screen and do not interfere with use of the screen, nor unduly extend the length of the tip and aspirator tube.

DESCRIPTION OF THE PREFERRED EMBODIMENTS

Figure 1:
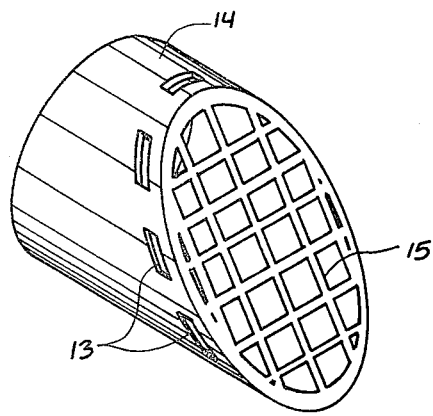
FIG. 1 is a front perspective view of the improved tip.

This disclosure relates to an improvement for use with a conventional aspirator, which is utilized by dentists and their assistants for removal of liquid and other materials from the mouth during dental procedures. The usual aspirator is in the form of a cylindrical tube 10. It is a metal tube having a slight bend (not shown) across its midsection. One end of the tube is typically formed with an inclined edge relative to the tube axis. The remaining end of the tube is normally perpendicular to the tube axis. The tube can be reversed, depending upon the manner of access desired in the patient's mouth. The tip shown in the drawings is designed specifically for use across the inclined edge of the tube, but it should be understood that a similar tip can be designed and placed across the perpendicular edge as well.

In use, one end of the tube 10 is fitted within the outer end of a suction hose (not shown) and the remaining or outer end of the tube is normally unobstructed and open for use within the mouth. It is common for the dentist or the assistant to maintain the open outer end of the aspirator in the mouth during the performing of dental procedures. A relatively large open diameter of the aspirator tube and the substantial vacuum pressure applied to it remove large quantities of water and liquids from the mouth, particularly during use of modern high speed drills and related equipment. However, this occasionally results in accidental engagement of inlays, crowns and other materials, which are then drawn through the aspirator to a remote vacuum pump. Retrieval of such materials is difficult and time consuming.

Figure 6:
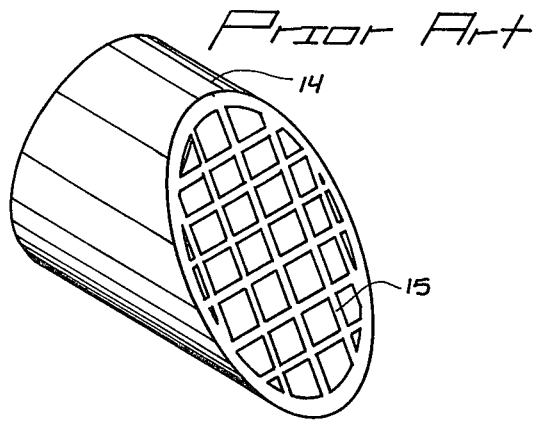
FIG. 6 is a front elevation view of a prior art device.
Figure 2:
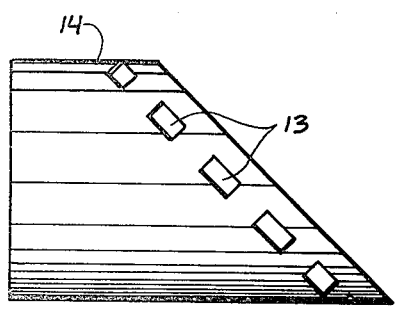
FIG. 2 is a side elevation view.
Figure 3:
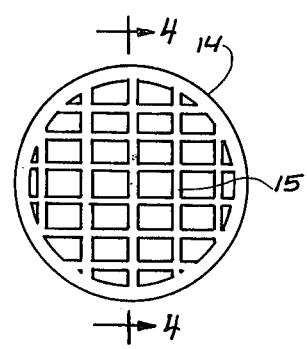
FIG. 3 is a front view.

FIG. 6 illustrates the prior art tip which has been used and sold by me in the past. It constitutes a molded tip with an integral molded screen across one end. The only openings at the outer end of this tip are through the screen mesh, which is located in a single flat plane. While this tip provided suitable protection against accidental engagement of larger articles within the mouth, it also posed a continuing problem of accidental attachment to soft mouth tissue, which was then drawn inwardly toward the aspirator tube. This attachment of the tip and tube to the mouth tissues is discomforting to a patient and occasionally results in minor pain or injury. The present improvement has been designed in an effort to overcome this problem.

The tip shown in FIGS. 1 through 4 is preferably molded by injection molding procedures. It is produced from a thermoplastic resin, such as polyethylene or other resins which are safe for use in the mouth and capable of being cold sterilized. The tip comprises a cylindrical sleeve 14 complementary to the outer cylindrical surface of the aspirator tube 10. The inside diameter of sleeve 14 is therefore substantially equal to the outer diameter of the tube 10. One end of sleeve 14 is open and unobstructed, presenting an edge that is perpendicular to the central axis of the sleeve. Its remaining end is enclosed by a transverse open mesh screen molded integrally with the sleeve and indicated by reference numeral 15. The screen 15 is located in a plane corresponding to the plane of the outer edge 11 across tube 10 (see FIG. 4). The angular position of the screen 15 enables it to fit adjacent to edge 11. The slight shoulder 12 within the sleeve 14 spaces screen 15 outward from the edge 11. The shoulder 12 accurately locates the tip and sleeve 14 on the end of the tube 10 and reinforces the walls of the sleeve 14 so that it properly remains in place and can be readily controlled during use of the aspirator 10.

The face of screens 15 is formed as a grid, having intersecting bars perpendicular to one another and forming interspersed apertures. The apertures provide minimum obstruction to permit normal passage of liquid into the aspirator tube, while preventing larger objects and solid materials from entering the tube 10 while the tip is in place on its outer end.

Figure 5:
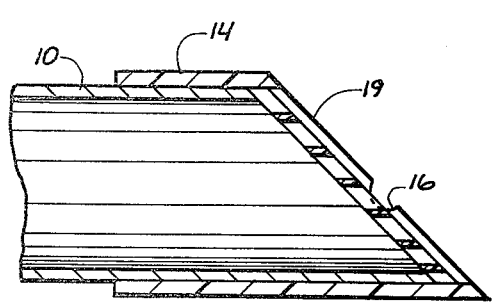
FIG. 5 is a sectional view similar to FIG. 4, showing a modification.
Figure 4:
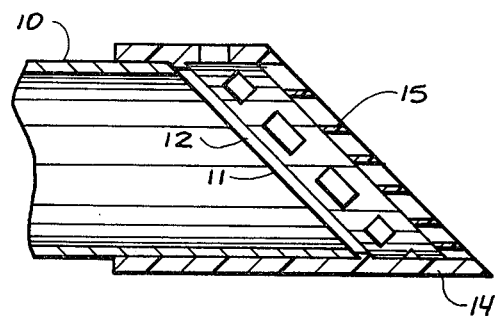
FIG. 4 is a fragmentary sectional view taken along line 4—4 in FIG. 3, showing the tip mounted on an aspirator tube.

Screen 15 can be either flush with the outer edge of the sleeve 14, as shown in FIG. 4, or can be slightly recessed and bounded by a peripheral bead 19, as shown in FIG. 5. The slight recess afforded by the beaded edge further minimizes direct contact of screen 15 by mouth tissue and results in more comfortable contact between the tip and the patient. It eliminates all sharp edges and corners.

As shown in FIGS. 1 through 4, a series of peripheral vents 13 are formed through the walls of sleeve 14 directly adjacent to screen 15. The vents 13 extend completely about the sleeve 14. They provide vacuum relief to the interior of the tip and aspirator tube, thereby preventing attachment of the tip to mouth tissue while in use. The vents 13 can either be molded during production of the tip, or formed within the tip subsequent to molding.

A second form of the improved tip is illustrated in FIG. 5. It again includes a cylindrical sleeve 14 complementary to tube 10. The outer edge of sleeve 14 is formed as a rounded bead 19, interrupted by transverse notches 16 for vent purposes. The screen 15 is recessed inwardly from the bead 19 and directly engages the outer end of tube 10.

The combination of the recessed screen 15 and side notches 16 provide clearance to assure against soft tissue being drawn across the tip end. Each notch overlaps the outer surface of screen 15 to assure constant venting even though the bead 19 might be covered by tissue at a given moment.

The tip as shown and described herein facilitates use of an aspirator and enables the user to insert the aspirator tube and tip into the mouth of a patient during delicate positioning procedures when one might otherwise hesitate to use the aspirator due to the danger of accidental loss of a valuable inlay, cap or filling. During normal use of the aspirator to withdraw water and saliva during preparation of teeth for filling, this tip assists in preventing the aspirator from accidentally engaging soft mouth tissues and becoming lodged in the mouth. The vacuum engagement of the soft tissue is eliminated by the lateral vents provided across the sleeve 14. The tip can be readily removed from the aspirator when it is desirable or necessary to evacuate larger solid materials from the mouth of the patient through the open tube end. No permanent attachment or screen is utilized.

This disclosure relates to a tip for an aspirator and is not directed to a saliva ejector. It serves the basic function of permitting the aspirator to withdraw liquid from the patient's mouth, while preventing solid items from being drawn to the mechanical vacuum pump unit to which an aspirator is connected. This prevents both accidental loss or damage and also insures against pump damage as well. The latter devices have been used by dentists for routine removal of saliva. They are normally not handheld and usually are placed near the front of the mouth. The saliva ejector is operated at a substantially low vacuum pressure and has a relatively small diameter in comparison to the modern aspirator tube. It will not normally receive large foreign objects and is not usually located in such close proximity to inlays, caps, or fillings so as to pose the same problem of accidental engagement and withdrawal of such materials. A saliva ejector is not normally connected to a pump unit subject to damage, but uses a venturi-type connection within an accessory water system. Very different problems are posed by use of these two different fluid removal systems.

Having described my invention, I claim:

1. The removable protective tip for placement over the axial outer end of a dental aspirator in the form of a rigid cylindrical tube with one end connected to a flexible hose and the remaining end having an outer edge, comprising:

a cylindrical sleeve molded of thermoplastic resin, said sleeve having an inner diameter substantially equal to the outer diameter of the tube;

one end of the sleeve being open;

the remaining end of the sleeve being partially closed by a transverse open-mesh screen molded integrally with said sleeve, said screen being located in a plane complementary to the plane of the outer edges of the tube, said screen being recessed inwardly from the outer edge of the sleeve about its remaining end;

and a plurality of open transverse vents formed through the sleeve immediately adjacent the screen, said vents being formed as inwardly directed notches through the outer edge of the sleeve and overlapping the outer surface of the screen.

* * * * *